United States Patent
Waki et al.

(10) Patent No.: US 9,332,958 B2
(45) Date of Patent: May 10, 2016

(54) ULTRASONIC DIAGNOSTIC APPARATUS AND METHOD OF DISPLAYING ULTRASONIC IMAGE

(75) Inventors: Koji Waki, Tokyo (JP); Hiroshi Kuribara, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 847 days.

(21) Appl. No.: 13/060,864

(22) PCT Filed: Jun. 22, 2009

(86) PCT No.: PCT/JP2009/061276
§ 371 (c)(1),
(2), (4) Date: Feb. 25, 2011

(87) PCT Pub. No.: WO2010/024023
PCT Pub. Date: Mar. 4, 2010

(65) Prior Publication Data
US 2011/0160590 A1     Jun. 30, 2011

(30) Foreign Application Priority Data
Aug. 25, 2008 (JP) ................... 2008-215368

(51) Int. Cl.
*A61B 8/14*     (2006.01)
*A61B 8/08*     (2006.01)
(Continued)

(52) U.S. Cl.
CPC . *A61B 8/08* (2013.01); *A61B 8/483* (2013.01); *A61B 8/485* (2013.01); *G01S 7/52036* (2013.01);
(Continued)

(58) Field of Classification Search
CPC .......... A61B 8/08; A61B 8/483; A61B 8/485; A61B 8/14; A61B 8/4461; A61B 8/466; A61B 8/4254; G01S 7/52036; G01S 7/52042; G01S 15/8993
See application file for complete search history.

(56) References Cited

U.S. PATENT DOCUMENTS 5,152,294 A * 10/1992 Mochizuki et al. ........... 600/459
7,901,357 B2 * 3/2011 Boctor et al. .................. 600/443
(Continued)

FOREIGN PATENT DOCUMENTS

| JP | 2000060853 | 2/2000 |
| JP | 2006271523 | 10/2006 |

(Continued)

OTHER PUBLICATIONS

"3D Elastography Using Freehand Ultrasound," Ultrasound in Med. & Bio., vol. 32, No. 4, pp. 529-545, 2006.*
(Continued)

*Primary Examiner* — Colin T Sakamoto
(74) *Attorney, Agent, or Firm* — Jones Robb, PLLC

(57) ABSTRACT

Provided is an ultrasonic diagnostic apparatus that constructs and displays a 3-dimensional elastic image showing the hardness or softness of a biological tissue of an object to be examined, and a method of displaying an ultrasonic image. The ultrasonic diagnostic apparatus is characterized by being provided with an elastic image constructing unit (24) that constructs 2-dimensional elastic image data on the basis of the strain or elasticity modulus acquired by the elasticity information calculating unit (23), an elastic volume data creating unit (26) that creates elastic volume data from plural sets of the 2-dimensional elastic image data, and 3-dimensional elastic image constructing unit (28) that constructs a 3-dimensional elastic image from the elastic volume data.

19 Claims, 12 Drawing Sheets

(51) Int. Cl.
*G01S 7/52* (2006.01)
*G01S 15/89* (2006.01)
*A61B 8/00* (2006.01)

(52) U.S. Cl.
CPC ......... *G01S 7/52042* (2013.01); *G01S 15/8993* (2013.01); *A61B 8/14* (2013.01); *A61B 8/4254* (2013.01); *A61B 8/4461* (2013.01); *A61B 8/466* (2013.01)

(56) References Cited

U.S. PATENT DOCUMENTS

2003/0171672 A1* 9/2003 Varghese et al. .............. 600/420
2006/0229513 A1 10/2006 Wakai
2010/0036243 A1* 2/2010 Matsumura .................. 600/438

FOREIGN PATENT DOCUMENTS

JP 2006288495 10/2006
JP 2008178500 8/2008
JP 2008-259555 * 10/2008

OTHER PUBLICATIONS

Ohbuchi et al., "Incremental 3D Ultrasound Imaging from a 2D scanner". Visualization in Biomedical Computer, Proceedings of First Conference on. IEEE. 1990. pp. 360-367.*

RadiologyInfo "Ultrasound—General". archived May 31, 2008, retrieved May 15, 2014 from <https://web.archive.org/web/20080531073755/http://www.radiologyinfo.org/en/info.cfm?pg=genus>.*

* cited by examiner

FIG.2
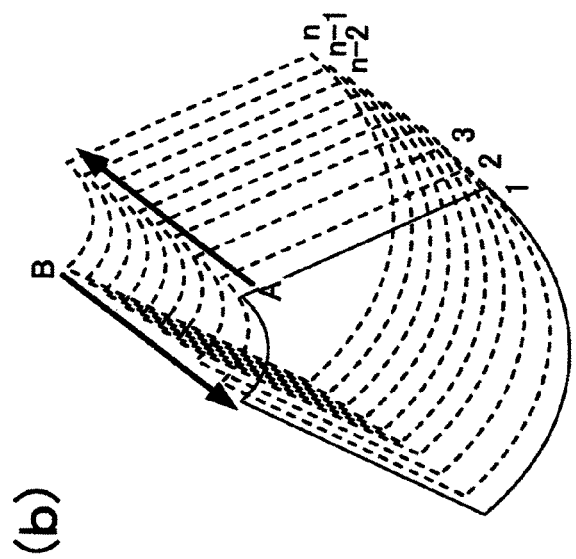
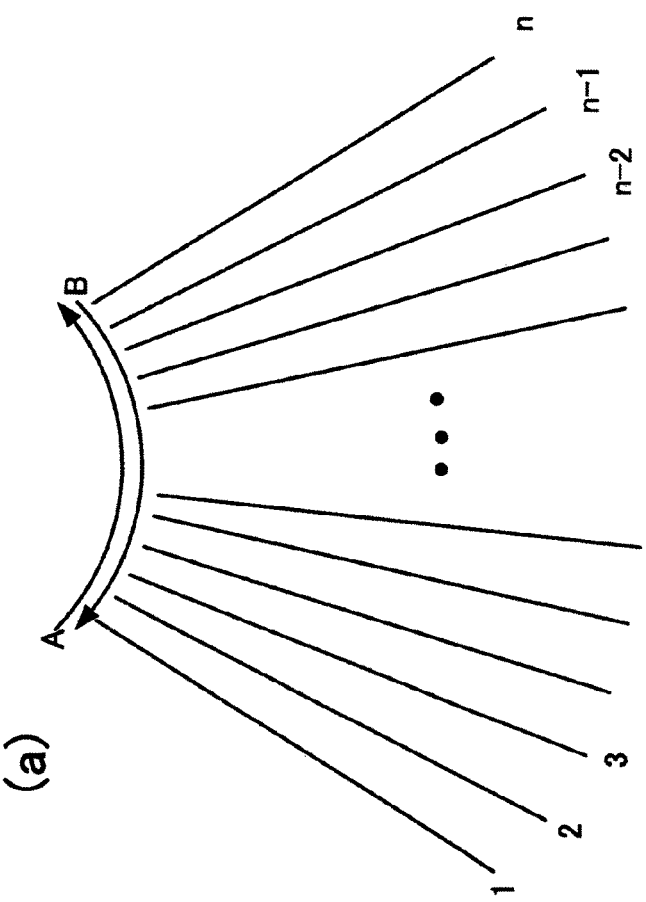

FIG.6
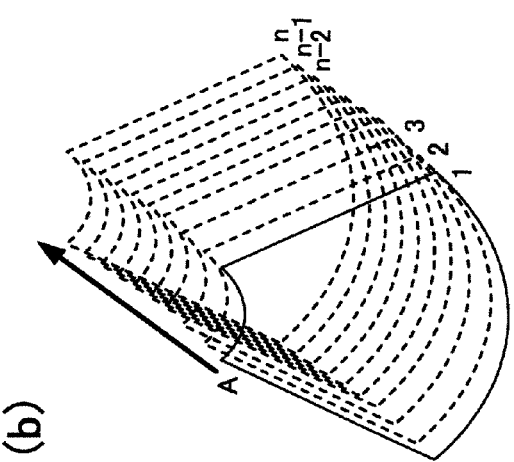
(a)
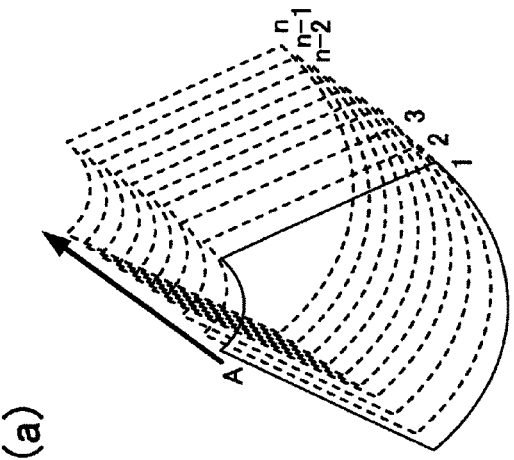
(b)
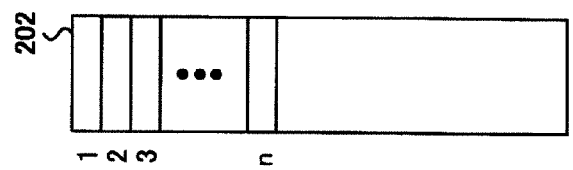
(c)
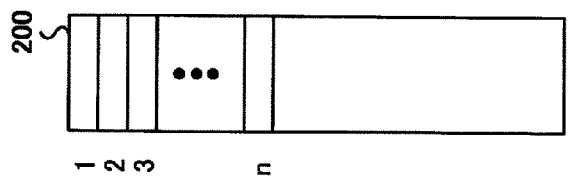
(d)

ULTRASONIC DIAGNOSTIC APPARATUS AND METHOD OF DISPLAYING ULTRASONIC IMAGE

FIELD OF THE INVENTION

The present invention relates to an ultrasonic diagnostic apparatus and the method of displaying an elastic image showing hardness or softness of biological tissues of an object to be examined using ultrasonic waves.

DESCRIPTION OF RELATED ART

An ultrasonic diagnostic apparatus transmits ultrasonic waves to the inside of the body of an object by an ultrasonic probe, constructs and displays an image such as a tomographic image based on the reception signals received from the biological tissues inside of the object. Also, it measures the reception signals received from the biological tissues in the object by the ultrasonic probe, and obtains displacement in the respective areas of the body from the RF signal frame data of the two reception signals measured at different times. Then it constructs an elastic image showing elasticity modulus of the biological tissues based on the displacement data (for example, Patent Document 1).

Also, it has a position sensor for measuring the position and tilt of the ultrasonic probe at the same time of transmitting and receiving ultrasonic waves, generates volume data from the positional information obtained by the position sensor and a plurality of 2-dimensional tomographic images, and displays a 3-dimensional tomographic image (for example, Patent Document 2).

PRIOR ART DOCUMENTS

Patent Document 1: JP-A-2000-060853
Patent Document 2: JP-A-2006-271523

However, the technique disclosed in Patent Document 1 only constructs a 2-dimensional elastic image and does not disclose construction of a 3-dimensional image in concrete terms. Therefore, construction of a 3-dimensional elastic image requires a tremendous amount of calculation and memory capacity, and is impossible to achieve merely by extending the technique for constructing a 3-dimensional tomographic image disclosed in Patent Document 2.

The objective of the present invention is to construct and display a 3-dimensional elastic image showing hardness or softness of biological tissues in an object.

BRIEF SUMMARY OF THE INVENTION

In order to achieve the above-mentioned objective, the present invention provides an ultrasonic diagnostic apparatus comprising:
an ultrasonic probe configured to transmit/receive ultrasonic waves to/from an object to be examined by transducers;
a transmission unit configured to transmit ultrasonic waves via the ultrasonic probe;
a reception unit configured to receive the reflected echo signals from the object;
an RF signal frame data storing unit configured to store the RF signal frame data based on the reflected echo signals received by the reception unit;
an RF signal frame data selecting unit configured to select at least two sets of RF signal frame data stored in the RF signal frame data storing unit;
an elasticity information calculation unit configured to calculate strain or elasticity modulus based on the selected RF signal frame data;
an elastic image constructing unit configured to construct a 2-dimensional elastic image data based on the strain or elasticity modulus acquired by the elasticity information calculation unit;
an elasticity volume data creating unit configured to create elasticity volume data from plural sets of 2-dimensional elastic image data; and
a 3-dimensional elastic image constructing unit configured to construct a 3-dimensional elastic image from the elastic volume data created by the elasticity volume data creating unit.

Accordingly, it is possible to construct a 3-dimensional elastic image showing hardness or softness of biological tissues of an object.

EFFECT OF THE INVENTION

In accordance with the present invention, it is possible to construct and display a 3-dimensional elastic image showing hardness or softness of biological tissues in an object.

BRIEF DESCRIPTION OF THE DRAWINGS

FIG. 2 shows storage pattern of tomographic image data related to the present invention.
FIG. 6 shows details of the RF signal frame data storing unit in a second embodiment of the present invention.

DETAILED DESCRIPTION OF THE INVENTION

First Embodiment

Inverse-Direction Correlation

Figure 1:
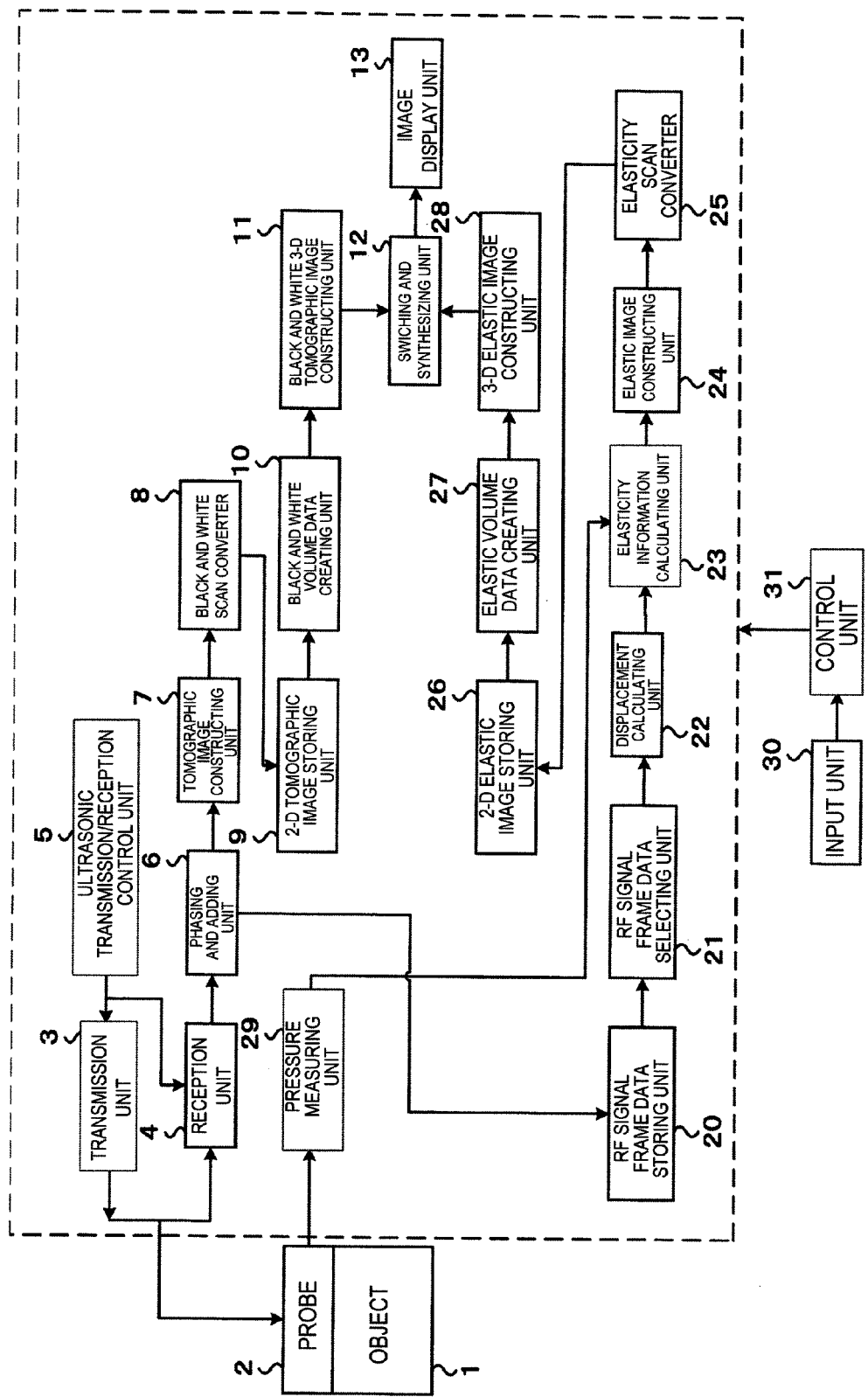
FIG. 1 shows a block diagram showing a general configuration of the present invention.

The ultrasonic diagnostic apparatus to which the present invention is applied will be described referring to FIG. 1. As shown in FIG. 1, the ultrasonic diagnostic apparatus comprises:
ultrasonic probe 2 to be used by applying to object 1;
transmission unit 3 configured to repeatedly transmit ultrasonic waves to object 1 via ultrasonic probe 2 at time intervals;
reception unit 4 configured to receive the reflected echo signals produced from object 1 in time series;

ultrasonic transmission/reception control unit 5 configured to control switching of transmission and reception of transmission unit 3 and reception unit 4; and phasing and adding unit 5 configured to perform phasing and adding the reflected echo signals received by reception unit 4.

Ultrasonic probe 2 is formed by disposing a plurality of transducers therein, and has a function to transmit/receive ultrasonic waves to/from object 1 via the transducers. It is capable of transmitting/receiving ultrasonic waves by mechanically vibrating the transducers in the direction orthogonal to their array direction. Also, ultrasonic probe 2 has a position sensor that measures tilt of the transducers at the same time as transmitting/receiving ultrasonic waves and outputs the measured tilt of the transducers as the frame number. It may have a plurality of transducers that are 2-dimensionally disposed therein and capable of electrically controlling the transmitting/receiving direction of the ultrasonic waves.

In this manner, ultrasonic probe 2 mechanically or electrically vibrates the transducers in the direction orthogonal to the array direction of the plurality of transducers, and transmits/receives ultrasonic waves. Transmission unit 3 generates transmitting pulses for generating ultrasonic waves by driving the transducers of ultrasonic probe 2. Transmission unit 3 has the function to set a focusing point of the transmitted ultrasonic waves at a certain depth. Also, reception unit 4 is for generating RF signals, i.e. reception signals by amplifying the reflected echo signals received by ultrasonic probe 2 at a predetermined gain. Ultrasonic transmission/reception control unit 5 controls transmission unit 3 and reception unit 4.

Phasing and adding unit 5 inputs the RF signals amplified in reception 4 and performs phase control, and generates RF signal frame data by forming ultrasonic beams with respect to one or more focusing points.

Tomographic image constructing unit 7 inputs the RF signal frame data from phasing and adding unit 6, and executes signal processing such as gain compensation, log compression, detection, edge enhancement or filtering so as to obtain tomographic image data. Also, black and white scan converter 8 performs coordinate system conversion of tomographic image data for displaying the tomographic image data synchronized With scanning of ultrasonic waves by the display system of image display unit 13.

2-dimensional tomographic image storing unit 9 stores the tomographic image data outputted from black and white scan converter 8 along with the frame numbers as shown in FIG. 2. Here, the plurality of transducers are mechanically vibrated in the direction orthogonal to the array their direction so as to transmit/receive ultrasonic waves, and the tomographic image data of n-frame is obtained with respect to the scan in A-direction or B-direction.

FIG. 2(*a*) shows 3-dimensional acquisition of tomographic image data assuming the 2-dimensional tomographic image data as one line in the frame direction. FIG. 2(*b*) shows 3-dimensional acquisition of 2-dimensional tomographic image data.

As shown in FIG. 2(*a*), the frame number is for corresponding the position (tilt) of a plurality of transducers to the tomographic image data. The first frame number of the scan in the A-direction is set as "1", and the last frame number is set as "n". The tomographic image data of frame number "1" is first stored in 2-dimensional tomographic image storing unit 9, then the tomographic image data of frame number "2" is stored in 2-dimensional tomographic image data storing unit 9. Then the tomographic image data of frame number "n" is finally stored in 2-dimensional tomographic image data storing unit 9. Also, by setting the first frame number of the scan in the B-direction as "n" and setting the last frame number as "1", tomographic image data is stored in 2-dimensional tomographic image data storing unit 9.

Black and white volume data creating unit 10 reads out tomographic image data for the portion of n-frame stored in 2-dimensional tomographic image storing unit 9, and creates black and white volume data by sequentially disposing the data for each scan plane. In this manner, black and white volume data for rendering which is the collection of tomographic image data in an object is created.

Black and white 3-dimensional tomographic image constructing unit 11 reads out black and white volume data from black and white volume data creating unit 10, and constructs a black and white 3-dimensional tomographic image by projecting the black and white volume data on a plane. In concrete terms, black and white 3-dimensional image constructing unit 11 acquires image information on each point of black and white volume data from the luminance value and opacity corresponding to the respective points (coordinates). Then it calculates the luminance value and opacity of the black and white volume data of the line of sight direction in the depth direction using an equation such as the one shown below, and constructs a black and white 3-dimensional tomographic image using the volume rendering method that gives contrasting density.

$$\alpha_{outi} = \alpha_{ini} + (1 - \alpha_{ini}) \times \alpha_i$$

$$C_{outi} = C_{ini} + (1 - \alpha_{ini}) \times \alpha_i \times C_i \qquad \text{[Equation 1]}$$

$\alpha_{outi}$: output of the i-th opacity
$\alpha_{ini}$: input of the i-th opacity
$\alpha_i$: the i-th opacity
$C_{outi}$: output of the i-th luminance value
$C_{ini}$: input of the i-th luminance value
$C_i$: the i-th luminance value While the volume rendering method is used above for constructing a black and white 3-dimensional tomographic image, other methods may be used such as the surface rendering method that gives contrasting density according to the tilt angle formed by the pixel in each point with respect to the plane corresponding to the view point position or the voxel method that gives contrasting density according to the depth of an object viewed from the view point position.

Also, the ultrasonic diagnostic apparatus comprises switching and synthesizing unit 12 that synthesizes a black and white 3-dimensional tomographic image and a color 3-dimensional elastic image to be described later, juxtaposes and switches the images, and image display unit 13 that displays a black and white 3-dimensional tomographic image, a color 3-dimensional elastic image and the composite image in which the black and white 3-dimensional tomographic image and the color 3-dimensional elastic image is synthesized.

Further, the ultrasonic diagnostic apparatus comprises RF signal frame data storing unit 20 that stores the RF signal frame data outputted from phasing and adding unit 6, RF signal frame data selecting unit 21 that selects at least two sets of RF signal frame data stored in RF signal frame data storing unit 20, displacement calculating unit 22 that measures displacement of biological tissues in object 1 from the two sets of RF signal frame data, elasticity information calculating unit 23 that acquires elasticity information such as strain or elasticity modulus from the displacement information measured in displacement measuring unit 22, elastic image constructing unit 24 that constructs 2-dimensional elastic image data from the strain or elasticity modulus calculated in elasticity information calculating unit 23, and elastic scan converter 25 that executes coordinate system conversion on the 2-dimensional elastic image data outputted from elastic image constructing unit 24 for displaying the data by the display system of image display unit 13.

In the present embodiment, the ultrasonic diagnostic apparatus further comprises 2-dimensional elastic image storing unit 26 that stores the 2-dimensional elastic image data outputted from elasticity scan converter 25, elastic volume data creating unit 27 that creates elastic volume data from plural sets of 2-dimensional elastic image data, and 3-dimensional elastic image constructing unit 28 that constructs a color 3-dimensional elastic image from the elastic volume data.

Also, the ultrasonic diagnostic apparatus comprises control unit 31 that controls the respective components, and input unit 30 that executes various inputs to control unit 31. Input unit 30 comprises devices such as a keyboard or trackball.

Figure 3:
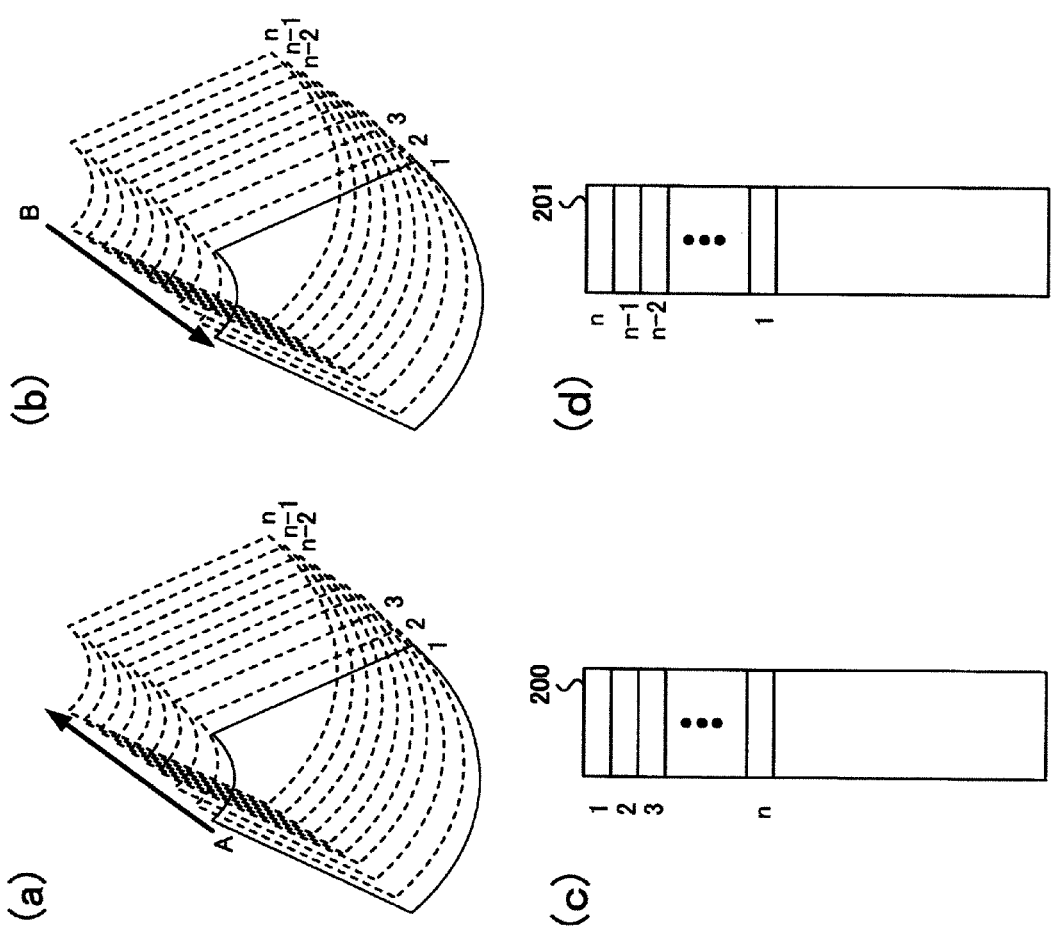
FIG. 3 shows details of an RF signal frame data storing unit in a first embodiment of the present invention.
Figure 4:
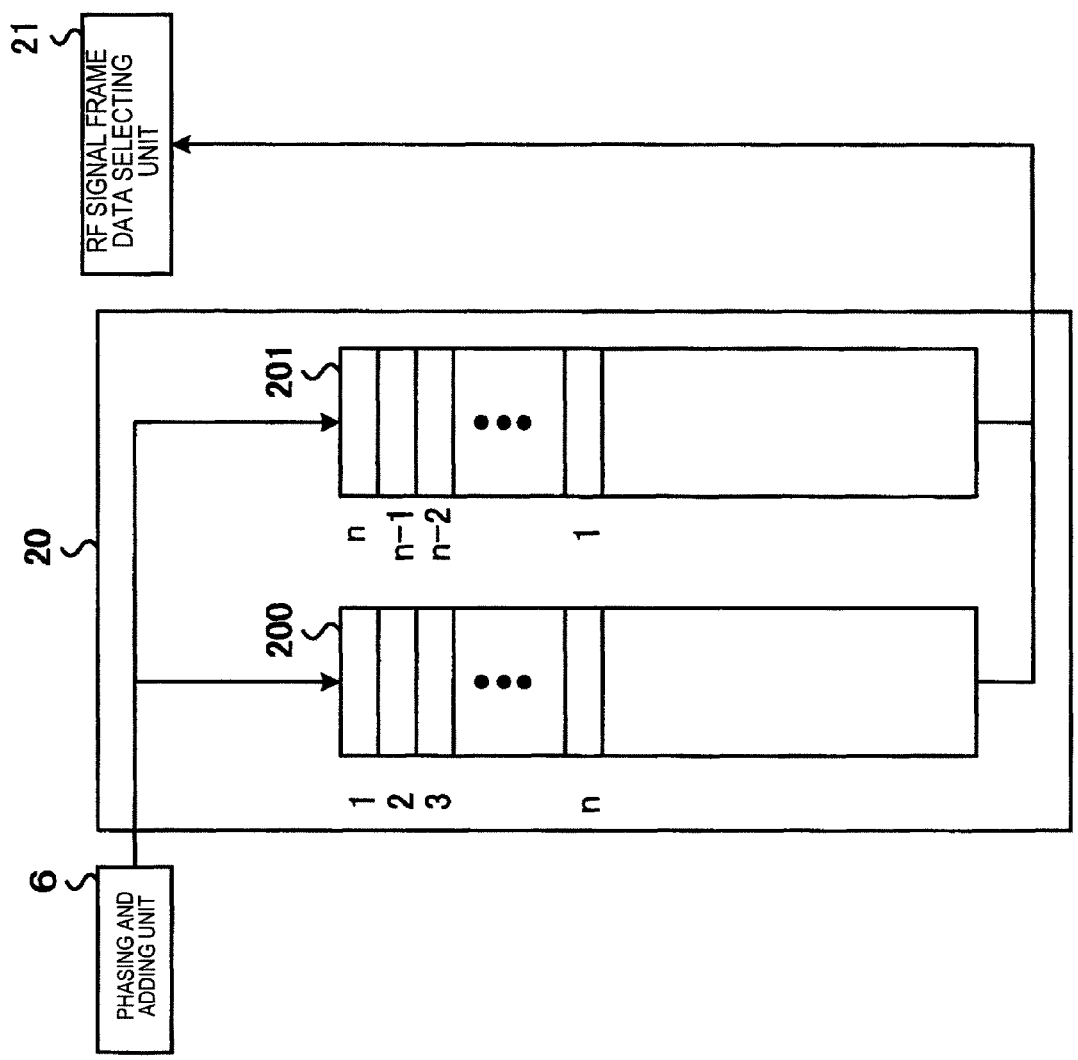
FIG. 4 shows details of the RF signal frame data storing unit in the first embodiment of the present invention.

RF signal frame data storing unit 20 sequentially stores the RF signal frame data generated from phasing and adding unit 6 in time series. FIG. 3 and FIG. 4 show the detail of RF signal frame data storing unit 20. In the present embodiment, RF signal frame data storing unit 20 has storage media 200 that stores the RF signal frame data related to the scan in the A-direction and storage media 201 that stores the RF signal frame data related to the scan in the B-direction.

FIG. 3(a) shows the relationship between the RF signal frame data of the scan in the A-direction and the frame number, and FIG. 3(c) shows the storage pattern of storage media 200 of RF signal frame data storing unit 20 that stores the RF signal frame data of the scan in the A-direction by corresponding the data to the frame numbers. FIG. 3(b) shows the relationship between the RF signal frame data of the scan in the B-direction and the frame numbers, and FIG. 3(d) shows the pattern of another storage media 201 of RF signal frame data storing unit 20 that stores the RF signal frame data of the scan in the B-direction by corresponding the data to the frame numbers.

Storage media 200 stores RF signal frame data by setting the first frame number of the scan in the A-direction as "1" and setting the last frame number as "n". Concretely, the RF signal frame data having frame number "1" of the scan in the A-direction is first stored in storage media 200, and then the RF signal frame data having frame number "2" is stored in storage media 200. Then the RF signal frame data having frame number "n" is finally stored in storage media 200.

Storage media 201 stores the RF signal frame data by setting the first frame number of the scan in the B-direction as "n" and setting the last frame number as "1". Concretely, the RF signal frame data "n" of the scan in the B-direction having frame number is first stored in storage media 201, and then the RF signal frame data having frame number "n−1" is stored in storage media 201. Then the RF signal frame data having frame number "1" is finally stored in storage media 201.

While RF signal frame data storing unit 20 has two storage media 200 and 201 above, RF signal frame data may also be sorted and stored in one storage media.

As shown in FIG. 4, RF signal frame data selecting unit 21 selects the RF signal frame data of frame number "N" stored in storage media 200 of RF signal frame data storing unit 20. N is an integer which is greater or equal to 1 and less or equal to "n". Then RF signal frame data selecting unit 21 selects the RF signal frame data of frame number "N" stored in storage media 201 which is the same frame number "N" of the RF signal frame data read out from storage media 200.

Then displacement measuring unit 22 executes one-dimensional or two dimensional correlation processing from the selected RF signal frame data of frame number "N", and obtains one-dimensional or two-dimensional displacement distribution related to the displacement or moving vector, i.e. the direction and size of the displacement in the biological tissues corresponding to each point of the RF signal frame data. Here, the block matching method is used for detecting the moving vector. The block matching method divides an image into blocks formed by, for example M×M pixels, focuses on a block within the region of interest, searches the block which is most approximated to the focused block from the previous frame, and executes the process to determine the sample value by predictive coding, i.e. difference referring to the searched block.

Elastic information calculating unit 23 calculates strain or elasticity modulus of the biological tissues corresponding to each point (coordinates) on the image from the measured value outputted from displacement measuring unit 22 such as the moving vector and the pressure value outputted from pressure measuring unit 26, and generates elasticity information. At this time, the strain is calculated by performing spatial differentiation on the distance, for example displacement of the biological tissue. Also, in the case of calculating elasticity modulus in elasticity information calculating unit 23, the pressure information acquired by pressure measuring unit 29 connected to a pressure sensor (not shown in the diagram) of ultrasonic probe 2 is outputted to elasticity information calculating unit 23. Elasticity modulus is calculated by dividing variation of the pressure by variation of the strain.

For example, by setting the displacement measured by displacement measuring unit 22 as L(X) and the pressure measured by pressure measuring unit 29 as P(X), since strain $\Delta S(X)$ can be calculated by performing spatial differentiation on L(X), elasticity modulus can be obtained using the equation: $\Delta S(X) = L(X)/\Delta X$. Also, Young's modulus Ym(X) of elasticity modulus is calculated by the equation: $Ym = (\Delta P(X))/\Delta S(X)$. Since elasticity modulus of the biological tissue corresponding to each point of an image can be obtained by this Young's modulus Ym, a 2-dimensional elastic image can be continuously acquired. Young's modulus is the ratio of simple tensile stress applied to an object to strain generated parallel to the tensile.

Elastic image constructing unit 24 executes various image processing such as the smoothing process within the coordinate plane, contrast optimization process or the smoothing process in the time axis direction among the frames with respect to the calculated elasticity value (strain, elasticity modulus, etc.), and constructs 2-dimensional elastic image data.

Elastic scan converter 25 has the function to execute coordinate system conversion on the 2-dimensional elastic image data outputted from elastic image constructing unit 24 for displaying by the scan method of image display unit 13. 2-dimensional elastic image storing unit 26 stores the 2-dimensional elastic image data along with frame number "N".

In this manner, as shown in FIG. 4, RF signal frame data selecting unit 21 selects the RF signal frame data of the same frame numbers "1"~"n" stored in storage media 200 and storage media 201 of RF signal frame data storing unit 20 respectively, and executes a series of processing in displacement measuring unit 22, elasticity information calculating unit 23, elastic image constructing unit 24 and elastic scan converter 25 as mentioned above.

Figure 5:
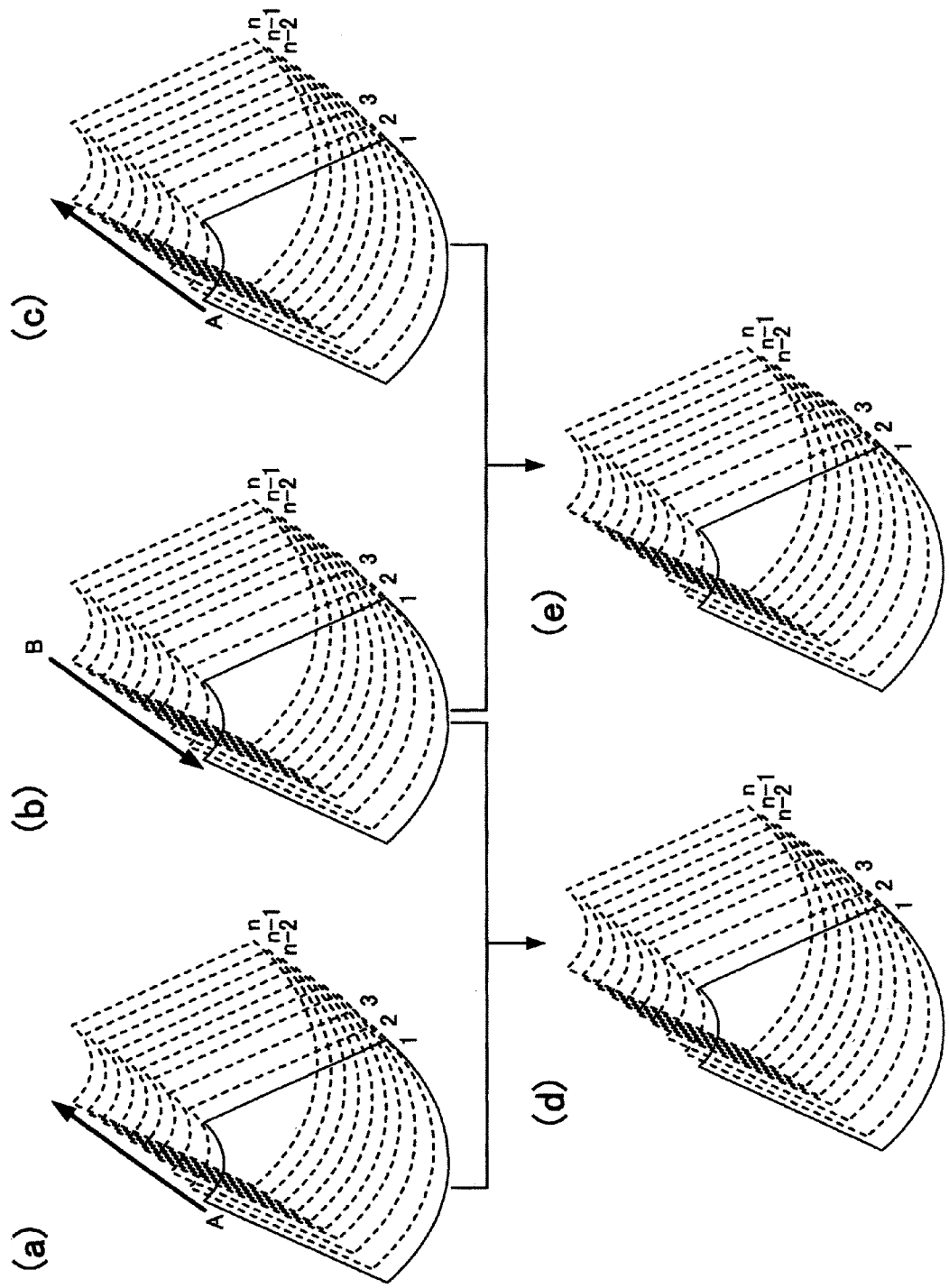
FIG. 5 shows the pattern for creating 2-dimensional elastic image data in the first embodiment of the present invention.

2-dimensional elastic image storing unit 26 stores the 2-dimensional elastic image data of a series of frame numbers "1"~"n". FIG. 5 shows the pattern for creating the 2-dimensional elastic image data of frame numbers "1"~"n". FIGS. 5(a) and (b) show the pattern that the RF signal frame data of frame numbers "1"~"n" in the A-direction or B-direction is read out from storage media 200 and storage media 201, and FIG. 5(d) shows the condition that the 2-dimensional elastic image data of frame numbers "1"~"n" is stored in 2-dimensional elastic image storing unit 26.

As shown in FIG. 5(c), in the case that the scanning is newly performed in the A-direction, the RF signal frame data of frame numbers "1"~"n" stored in storage media 200 is re-written as the RF signal frame data of frame numbers "1"~"n" that is newly scanned in A-direction. Then as shown in FIGS. 5(b) and (c), the RF signal frame data of the same frame numbers "1"~"n" in the A-direction and B-direction is read out from storage media 200 and storage media 201, elasticity calculation is performed in the same pattern as in FIG. 5(d) as shown in FIG. 5(e), and the 2-dimensional elastic image data of frame numbers "1"~"n" is stored in 2-dimensional elastic image storing unit 26. Also, the same procedure is to be carried out also when the scan is newly executed in B-direction that the scanning in A-direction and B-direction is sequentially repeated and the 2-dimensional elastic image data of frame numbers "1"~"n" is sequentially stored in 2-dimensional elastic image storing unit 26.

Elastic volume data creating unit 27 creates elasticity volume data from plural sets of 2-dimensional elastic image data. The 2-dimensional elastic image data for the portion of n-frame stored in 2-dimensional elastic image storing unit 26 is read out, and the elastic volume data is created by sequentially disposing the data for each scan plane. In this manner, the elastic volume data for rendering which is the collection of 2-dimensional elastic image data in the object is constructed.

3-dimensional elastic image constructing unit 28 acquires image information on each point of the elastic volume data from the elasticity value (any one of strain, elasticity modulus, etc.) and the opacity corresponding to the respective points, and constructs a 3-dimensional elastic image. For example, a 3-dimensional elastic image is constructed using the volume rendering method that calculates, in the depth direction, the elasticity value of the elastic volume data of the view point direction. This view point direction is the same direction as the view point direction in the volume rendering process, etc. in black and white 3-dimensional tomographic image constructing unit 11.

$$\alpha_{outi} = \alpha_{ini} + (1 - \alpha_{ini}) \times \alpha_i$$

$$E_{outi} = E_{ini} + (1 - \alpha_{ini}) \times \alpha_i \times E_i \quad \text{[Equation 2]}$$

$\alpha_{outi}$: output of the i-th opacity
$\alpha_{ini}$: input of the i-th opacity
$\alpha_i$: the i-th opacity
$E_{outi}$: output of the i-th elasticity value
$E_{ini}$: input of the i-th elasticity value
$E_i$: the i-th elasticity value Also, 3-dimensional elastic image constructing unit 28 appends light's three primary colors, i.e. red (R) value, green (G) value and blue (B) value to the image information that configure a 3-dimensional elastic image. The 3-dimensional elastic image constructing unit 28 appends, for example red color code to the place having greater strain or smaller elasticity modulus compared to the surrounding area, and appends blue color to the place having smaller strain or greater elasticity modulus compared to the surrounding area.

(Parallel Display/Superimposing Display)

Switching and synthesizing unit 12 is configured comprising an image memory, image processing unit and image selecting unit. Here, the image memory stores the black and white 3-dimensional tomographic image outputted from black and white 3-dimensional tomographic image constructing unit 11 and the color 3-dimensional elastic image outputted from 3-dimensional elastic image constructing unit 28 along with time information.

Also, the image processing unit synthesizes the black and white 3-dimensional tomographic image data stored in the image memory and the color 3-dimensional elastic image data by changing the synthesis ratio. Image processing unit reads out the black and white 3-dimensional tomographic image data and the color 3-dimensional elastic image data at the same view point position from the image memory. While the image processing unit synthesizes the black and white 3-dimensional tomographic, image data and the color 3-dimensional elastic image data, since the black and white 3-dimensional tomographic image data and the color 3-dimensional elastic image data is the image data after executing the volume rendering method, each set of data is actually added 2-dimensionally.

For example, as shown in the equations below, red (R) value, green (G) value and blue (B) value of the color 3-dimensional elastic image data and red (R) value, green (G) value and blue (B) value of the black and white 3-dimensional tomographic image data is added respectively in each point. In addition, α is the coefficient which is greater or equal of 0 and less or equal of 1, and can be set as desired via input unit 30.

$$\begin{aligned}
\text{(Composite image data } R\text{)} = \\
\alpha \times (\text{color 3-}D \text{ elastic image data } R) + (1 - \alpha) \times \\
(\text{black and white 3-}D \text{ tomographic image data } R) \\
\text{(Composite image data } G\text{)} = \\
\alpha \times (\text{color 3-}D \text{ elastic image data } G) + (1 - \alpha) \times \\
(\text{black and white 3-}D \text{ tomographic image data } G) \\
\text{(Composite image data } B\text{)} = \\
\alpha \times (\text{color 3-}D \text{ elastic image data } B) + (1 - \alpha) \times \\
(\text{black and white 3-}D \text{ tomographic image data } B)
\end{aligned} \quad \text{[Equation 3]}$$

For example, by setting the above-mentioned α as 0 or 1, it is possible to extract only the black and white 3-dimensional tomographic image data or the color 3-dimensional elastic image data. The image selecting unit selects the image to be displayed on image display unit 13 from among the black and white 3-dimensional tomographic image data or color 3-dimensional elastic image data in the volume memory or the composite image data in the image processing unit.

Image display unit 13 displays the composite image synthesized by switching and synthesizing unit, black and white 3-dimensional tomographic image or color 3-dimensional elastic image in parallel.

As described above, in accordance with the present embodiment, it is possible to construct and display a 3-dimensional elastic image showing hardness or softness of biological tissues in an object.

Second Embodiment

Correlation in the Same Direction

Next, the second embodiment will be described referring to FIG. 1 and FIGS. 6~8. The difference from the first embodiment is that the 2-dimensional elastic image data is created using the RF signal frame data of the scan in the same direction.

Figure 7:
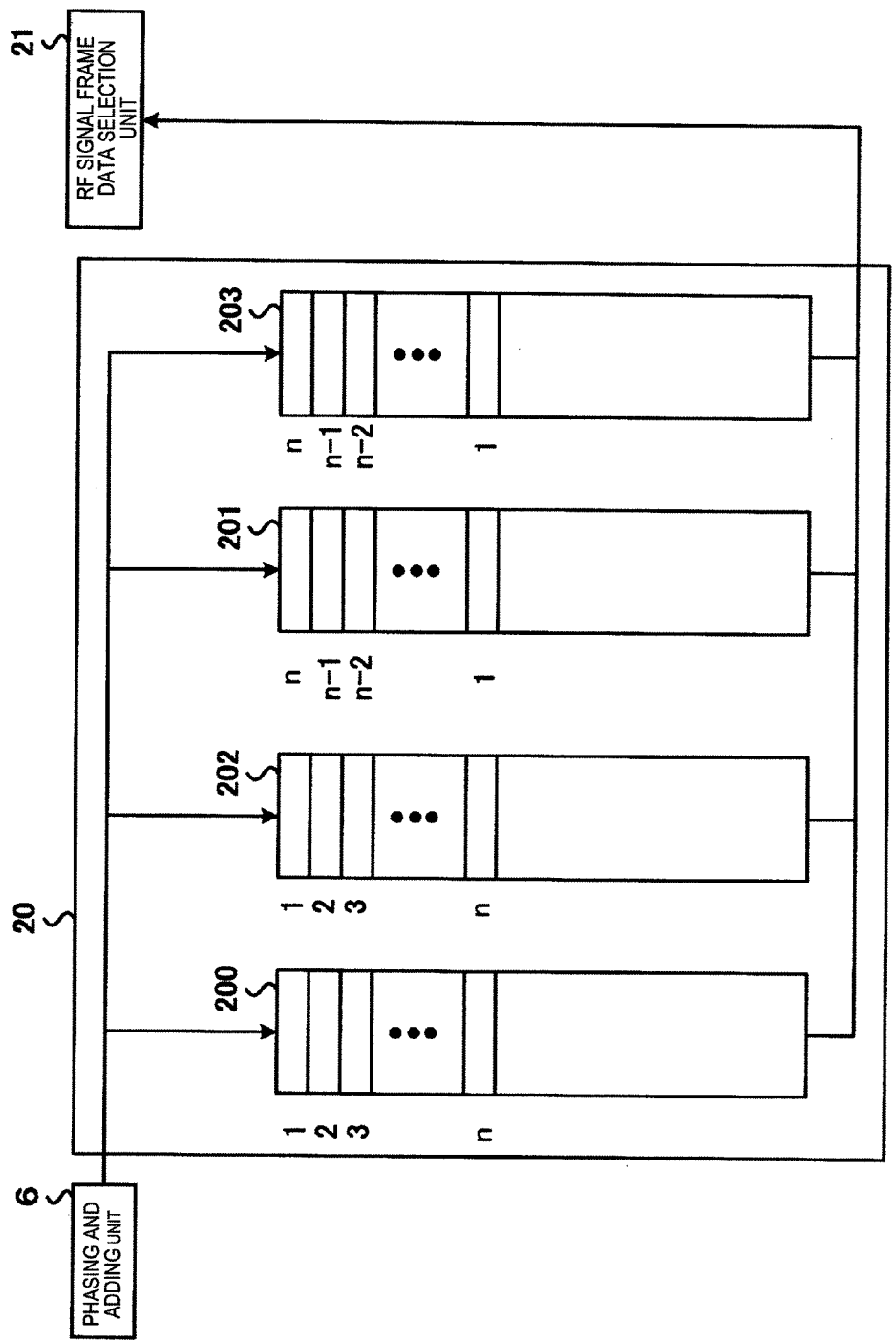
FIG. 7 shows details of the RF signal frame data storing unit in the second embodiment of the present invention.

FIG. 6 shows an example of storage media 200 and storage media 201 that stores the RF signal frame data of the scan in the A-direction. Storage pattern of storage media 200~203 is omitted here since it is the same as in the first embodiment. In concrete terms, as shown in FIG. 7, RF signal frame data storing unit 20 comprises storage media 200 and storage media 202 that store the RF signal frame data of the scan in the A-direction, and storage media 201 and storage media 203 that store the RF signal frame data of the scan in the B-direction.

Storage media 202 stores the RF signal frame data of frame numbers "1"~"n" of the scan in the A-direction which is the next set of the RF signal frame data stored in storage media 200. Storage media 203 stores the RF signal frame data of frame numbers "1"~"n" of the next scan in the B-direction which is the next set of the RF signal frame data stored in storage media 201.

Figure 8:
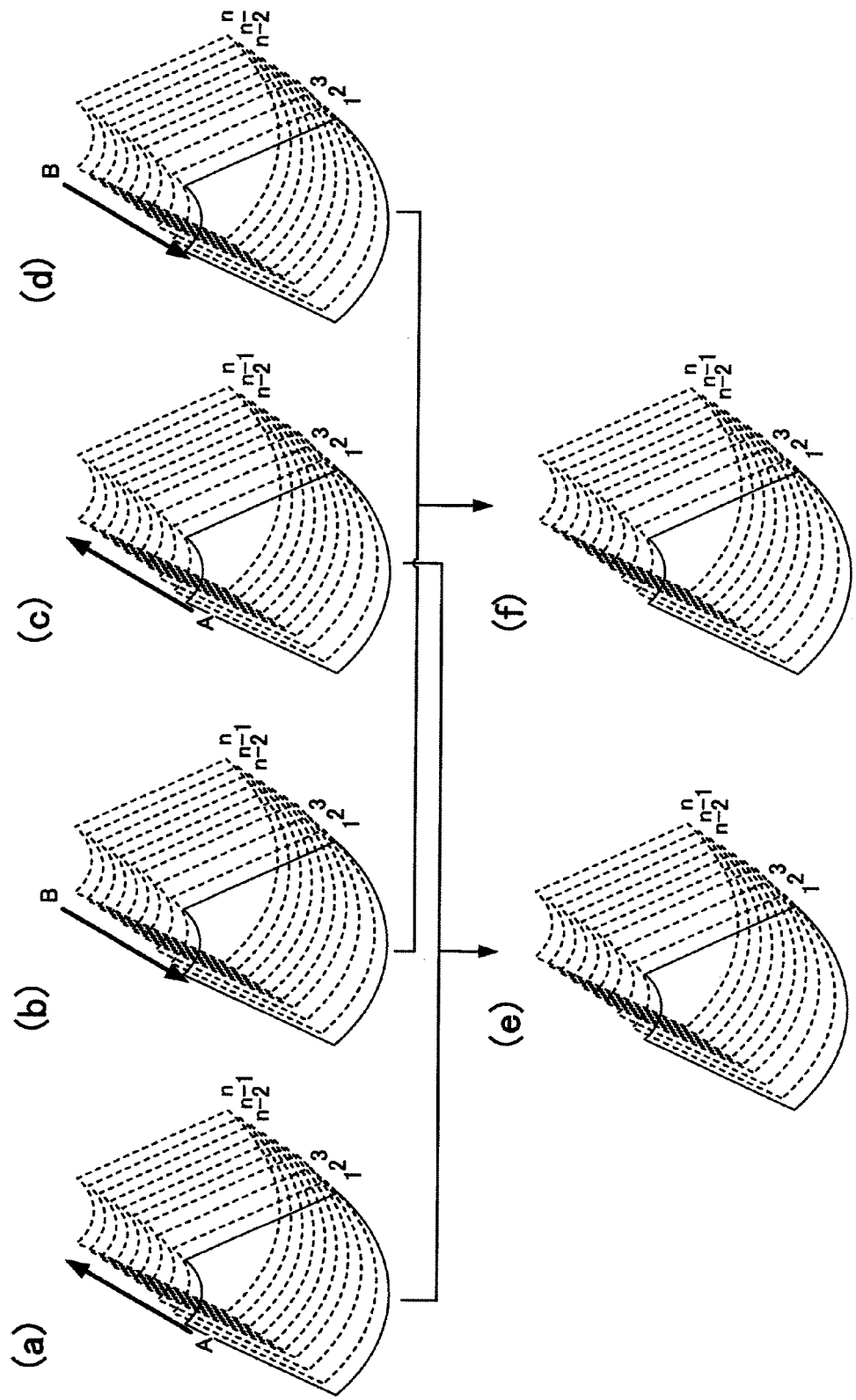
FIG. 8 shows the pattern for creating 2-dimensional elastic image data in the first embodiment of the present invention.

FIG. 8 shows the pattern for creating the 2-dimensional elastic image data of frame numbers "1"~"n". As shown in FIGS. 8(a) and (c), the RF signal frame data of frame numbers "1"~"n" in A-direction is read out from storage media 200 and storage media 202. In concrete terms, as shown in FIG. 7, RF signal frame data selecting unit 21 selects the RF signal frame data having the same frame numbers "1"~"n" stored in storage media 200 and storage media 202 of RF signal frame data storing unit 20 respectively. Then RF signal frame data selecting unit 21 constructs 2-dimensional elastic image data via displacement measuring unit 22, elasticity information calculating unit 23, elastic image constructing unit 24 and elasticity scan converter 25. The explanation on displacement measuring unit 22, elasticity information calculating unit 23, elastic image constructing unit 24 and elasticity scan converter 25 will be omitted here since they is the same as in the first embodiment. 2-dimensional elastic image storing unit 26 then stores the 2-dimensional elastic image data of a series of frame numbers "1"~"n" as shown in FIG. 8(e).

Also, as shown in FIGS. 8(b) and (d), the RF signal frame data of frame numbers "1"~"n" in the B-direction is read out from storage media 201 and storage media 203. In concrete terms, as shown in FIG. 7, RF signal frame data selecting unit 21 selects the RF signal frame data having the same frame numbers "1"~"n" stored in storage media 201 and storage media 203 of RF signal frame data storing unit 20 respectively. Then it constructs 2-dimensional elastic image data via displacement measuring unit 22, elasticity information calculating unit 23, elastic image constructing unit 24 and elasticity scan converter 25. 2-dimensional elastic image storing unit 26 stores the 2-dimensional elastic image data of a series of frame numbers "1"~"n" as shown in FIG. 8(f).

Then elastic volume data creating unit 27 creates elastic volume data from plural sets of 2-dimensional elastic image data. The 2-dimensional elastic image data for the portion of n-frame stored in 2-dimensional elastic image storing unit 26 is read out, and elastic volume data is created by the data being sequentially disposed for each scan plane. In this manner, the elastic volume data for rendering which is the collection of 2-dimensional elastic image data of an object is constructed.

Also, 3-dimensional elastic image constructing unit 28 acquires image information on each point of the elasticity volume data from the elasticity value (any one of strain, elasticity modulus, etc) and the opacity corresponding to the respective points, and constructs a 3-dimensional elastic image. Explanation on 3-dimensional elastic image constructing unit 28 is omitted here since it is the same as in the first embodiment.

As mentioned above, in accordance with the present embodiment, it is possible to construct and display a 3-dimensional elastic image showing hardness or softness of biological tissues of an object.

Third Embodiment

One Storage Media

Next, the third embodiment will be described referring to FIGS. 1 and 9. The difference from the first and second embodiments is that RF signal frame data storing unit 20 has one storage media.

Figure 9:
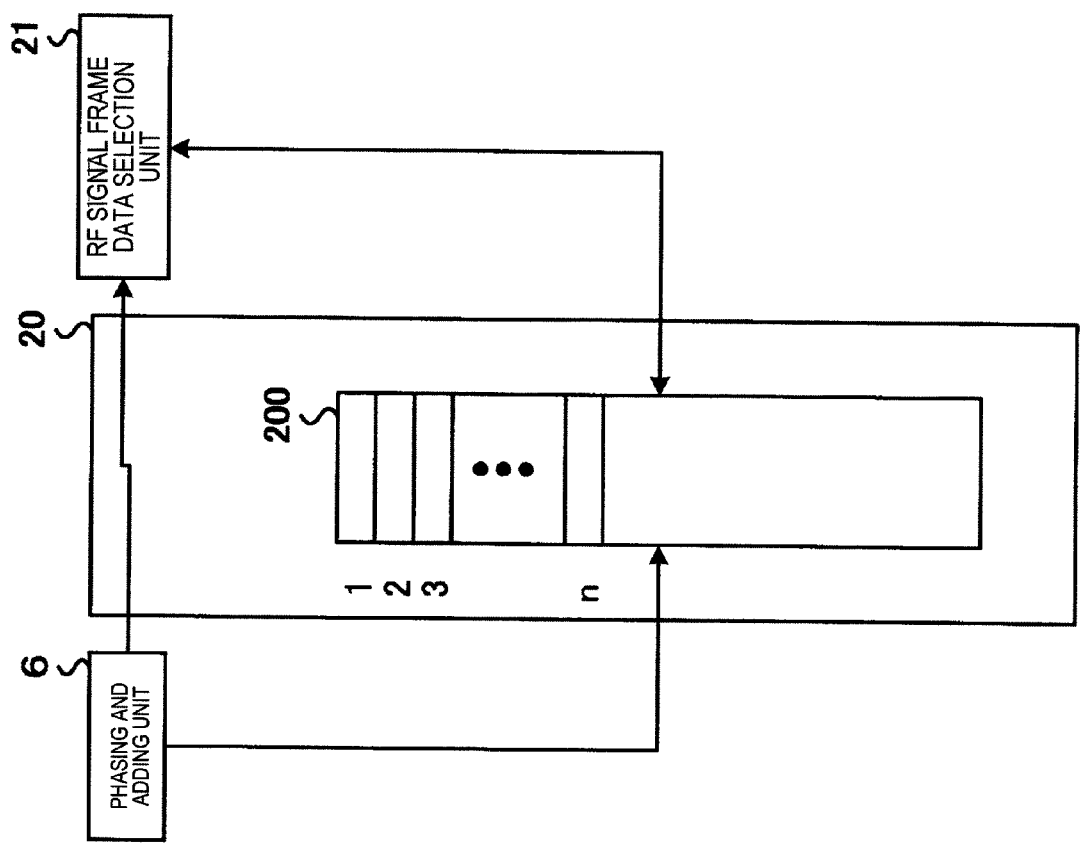
FIG. 9 shows a third embodiment of the present invention.

As shown in FIG. 9, RF signal frame data storing unit 20 comprises storage media 200 that stores the RF signal frame data of the scan in the A-direction. The RF signal frame data of frame number "1" of the scan in the A-direction is first stored in storage media 200, and the RF signal frame data of frame number "2" is next stored in storage media 200. Then the RF signal frame data of frame number "n" is finally stored in storage media 200.

Then new RF signal frame data of the next scan in the A-direction is directly outputted to RF signal frame data selecting unit 21 from phasing and adding unit 6. RF signal frame data selecting unit 21 reads out the RF signal frame data having the same frame numbers "1"~"n" as the RF signal frame data of the frame numbers "1"~"n" that is newly outputted from phasing and adding unit 6 respectively from storage media 200. Then RF signal frame data read out from storage media 200 by RF signal frame data selecting unit 21 is replaced by the new RF signal frame data and stored in storage media 200.

Based on the two sets of RF signal frame data of the respective frame numbers "1"~"n" selected by RF signal frame data selecting unit 21, 2-dimensional elastic image data is constructed via displacement measuring unit 22, elasticity information calculating unit 23, elastic image constructing unit 24 and elasticity scan converter 25. The explanation on displacement measuring unit 22, elasticity information calculating unit 23, elastic image constructing unit 24 and elasticity scan converter 25 will be omitted here since they is the same as in the first embodiment. 2-dimensional elastic image storing unit 26 stores the 2-dimensional elastic image of a series of frame numbers "1"~"n".

Then elastic volume data creating unit 27 creates elastic volume data from plural sets of 2-dimensional elastic image data. It reads out the 2-dimensional elastic image data for the portion of n-frame stored in 2-dimensional elastic image storing unit 26, and creates the elastic volume data by sequentially disposing them for each scan plane. In this manner, elastic volume data for rendering which is the collection of 2-dimensional elastic image data of an object is constructed.

Also, 3-dimensional elastic image constructing unit 28 acquires image information on each point of elastic volume data from the elasticity value (any one of strain, elasticity modulus, etc.) and the opacity corresponding to the respective points, and constructs a 3-dimensional elastic image. Detailed explanation on the 3-dimensional elastic image constructing unit 28 will be omitted here since it is the same as in the first embodiment.

In accordance with the present embodiment, it is possible to construct and display a 3-dimensional elastic image showing hardness or softness of biological tissues of an object by reducing capacity of the RF signal frame data storing unit.

Fourth Embodiment

3-Dimensional Image from Volume Data

Figure 10:
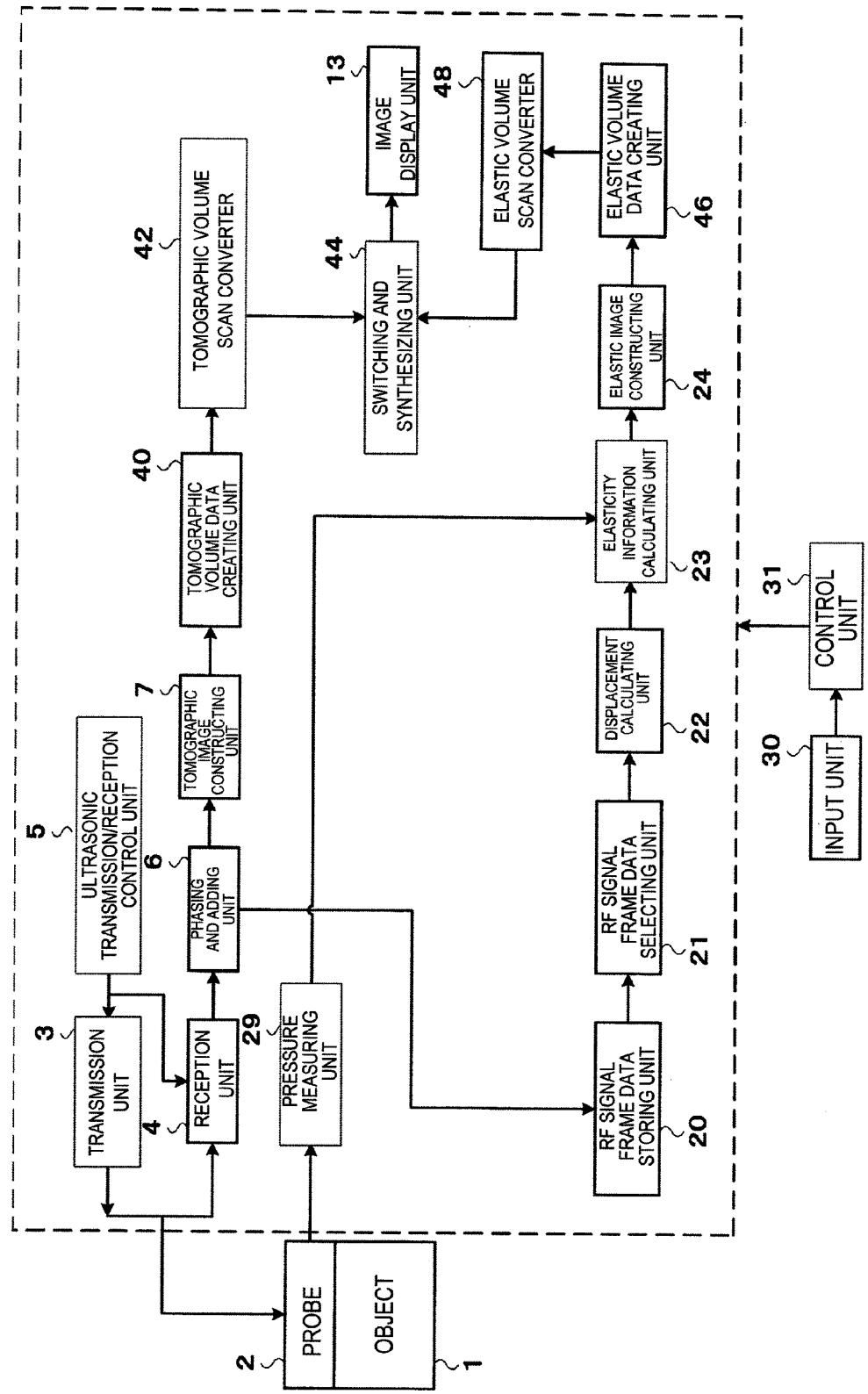
FIG. 10 shows a fourth embodiment of the present invention.

Next, the fourth embodiment will be described referring to FIG. 10. The difference from the first~third embodiments is that a 3-dimensional composite image is constructed from tomographic volume data and elastic volume data.

The ultrasonic diagnostic apparatus to which the present invention is applied will be described referring to FIG. 10. As shown in FIG. 10, the ultrasonic diagnostic apparatus comprises:

ultrasonic probe 2 configured to be used by applying to object 1;

transmission unit 3 configured to repeatedly transmit ultrasonic waves to object 1 via ultrasonic probe 2 at time intervals;

reception unit 4 configured to receive the time-series reflected echo signals generated from object 1;

ultrasonic transmission/reception control unit 5 configured to switch transmission and reception of transmission unit 3 and reception unit 4; and phasing and adding unit 6 configured to execute phasing and adding of the reflected echo signals received by reception unit 4. Detailed configuration of the apparatus is the same as in the first embodiment.

Tomographic image constructing unit 7 inputs RF signal frame data from phasing and adding unit 6, and executes signal processing such as gain compensation, log compression, detection, edge enhancement and filtering so as to obtain tomographic image data. Tomographic volume data creating unit 40 creates tomographic volume data by disposing tomographic image data in the scan direction while corresponding the data to frame numbers "1"~"n". Tomographic volume scan converter 42 executes coordinate system conversion of tomographic image volume data in order to display the tomographic volume data synthesized with ultrasonic scanning using the display system of image display unit 13.

The ultrasonic diagnostic apparatus further comprises:

RF signal frame data storing unit 20 configured to store the RF signal frame data outputted from phasing and adding unit 6;

RF signal frame data selecting unit 21 configured to select at least two sets of RF signal frame data stored in RF signal frame data storing unit 20;

displacement calculating unit 22 configured to measure displacement of biological tissues in object 1 from the two sets of RF signal frame data;

elasticity information calculating unit 23 configured to acquire elasticity information such as strain or elasticity modulus from the displacement information measured by displacement calculating unit 22;

elastic image constructing unit 24 configured to construct 2-dimensional elastic image data from the strain or elasticity modulus calculated by elasticity information calculating unit 23;

elastic volume data creating unit 41 configured to create elastic volume data from 2-dimensional elastic image data; and elastic volume scan converter 48 configured to execute coordinate system conversion of elasticity volume data. The detailed configuration of the devices except elastic volume data creating unit 41 and elastic volume scan converter 48 is the same as in the first embodiment.

Elastic volume data creating unit 46 creates 3-dimensional volume elastic volume data by disposing 2-dimensional elastic image data in the scan direction while corresponding the data to frame numbers "1"~"n". Elastic volume scan converter 48 executes coordinate system conversion of elastic volume data in order to display the elastic volume data synthesized with scanning of ultrasonic waves using the display system of image display unit 13.

Switching and synthesizing unit 44 comprises a volume memory and an image processing unit. Here, the volume memory is configured to store the tomographic volume data outputted from tomographic volume scan converter 42 and the elastic volume data outputted from elastic volume scan converter 48 along with time information.

The image processing unit is configured to synthesize the tomographic volume data stored in the volume memory and elastic volume data for each coordinate. The image processing unit further executes volume rendering on the composite volume data. In concrete terms, it acquires image information on each point of the composite volume data from the opacity, luminance value and elasticity value corresponding to the respective points.

$$\alpha_{outi} = \alpha_{ini} + (1 - \alpha_{ini}) \times \alpha_i$$

$$C_{outi} = C_{ini} + (1 - \alpha_{ini}) \times \alpha_i \times C_i$$

$$E_{outi} = E_{ini} + (1 - \alpha_{ini}) \times \alpha_i \times E_i \qquad \text{[Equation 4]}$$

Also, image processing unit appends light's three primary colors, i.e. red(R) value, green (G) value and blue (B) value on elastic volume data. The image processing unit appends, for example the red code to the place having greater strain or smaller elasticity modulus compared to the surrounding area, and appends the blue code to the place having smaller strain or greater elasticity modulus compared to the surrounding area. Then image display unit 13 displays the colored composite image.

In accordance with the present embodiment, it is possible to construct and display a 3-dimensional elastic image.

Fifth Embodiment

Increase Opacity of Hard Region

Next, the fifth embodiment will be described referring to FIG. 1. The difference from the first~fourth embodiments is that opacity is to be adjusted.

3-dimensional elastic image constructing unit 28 adjusts opacity of elastic volume data at the time of acquiring image information on each point of the elastic volume data from the elasticity value and the opacity corresponding to the respective points. In concrete terms, in the present embodiment, it raises the opacity of a hard region in elastic volume data having smaller strain or greater elasticity modulus (for example, 300 kPa and above) compared to the surrounding area.

Then 3-dimensional elastic image constructing unit 28 constructs a 3-dimensional elastic image using, for example the equation below by the volume rendering method which calculates an elasticity value of the elastic volume data of the view point direction in the depth direction. Here, β is the value that varies in accordance with strain or elasticity modulus. For example, β is the value in inverse proportion to the strain and is in proportion to the elasticity modulus.

$$\alpha_{outi} = \alpha_{ini} + (1 - \alpha_{ini}) \times \alpha_i + \beta_i$$

$$E_{outi} = E_{ini} + (1 - \alpha_{ini}) \times E_i \qquad \text{[Equation 5]}$$

Then the same process as in the first embodiment is carried out, and switching and synthesizing unit 12 synthesizes the black and white 3-dimensional tomographic image data stored in the image memory and color elastic image data by changing the synthesizing ratio so as to display the image on image display unit 13. Image display unit 13 displays the image which is synthesized by switching and synthesizing unit 12, a black and white 3-dimensional tomographic image or a color 3-dimensional elastic image.

In accordance with the present embodiment, since a hard region is displayed with high opacity, it is possible to execute display by emphasizing a diseased area such as a tumor.

Sixth Embodiment

Selecting Display

Next, the sixth embodiment will be described referring to FIG. 1, FIG. 11 and FIG. 12. The difference from the first~fifth embodiments is that 3-dimensional elastic image can be constructed partially.

Figure 11:
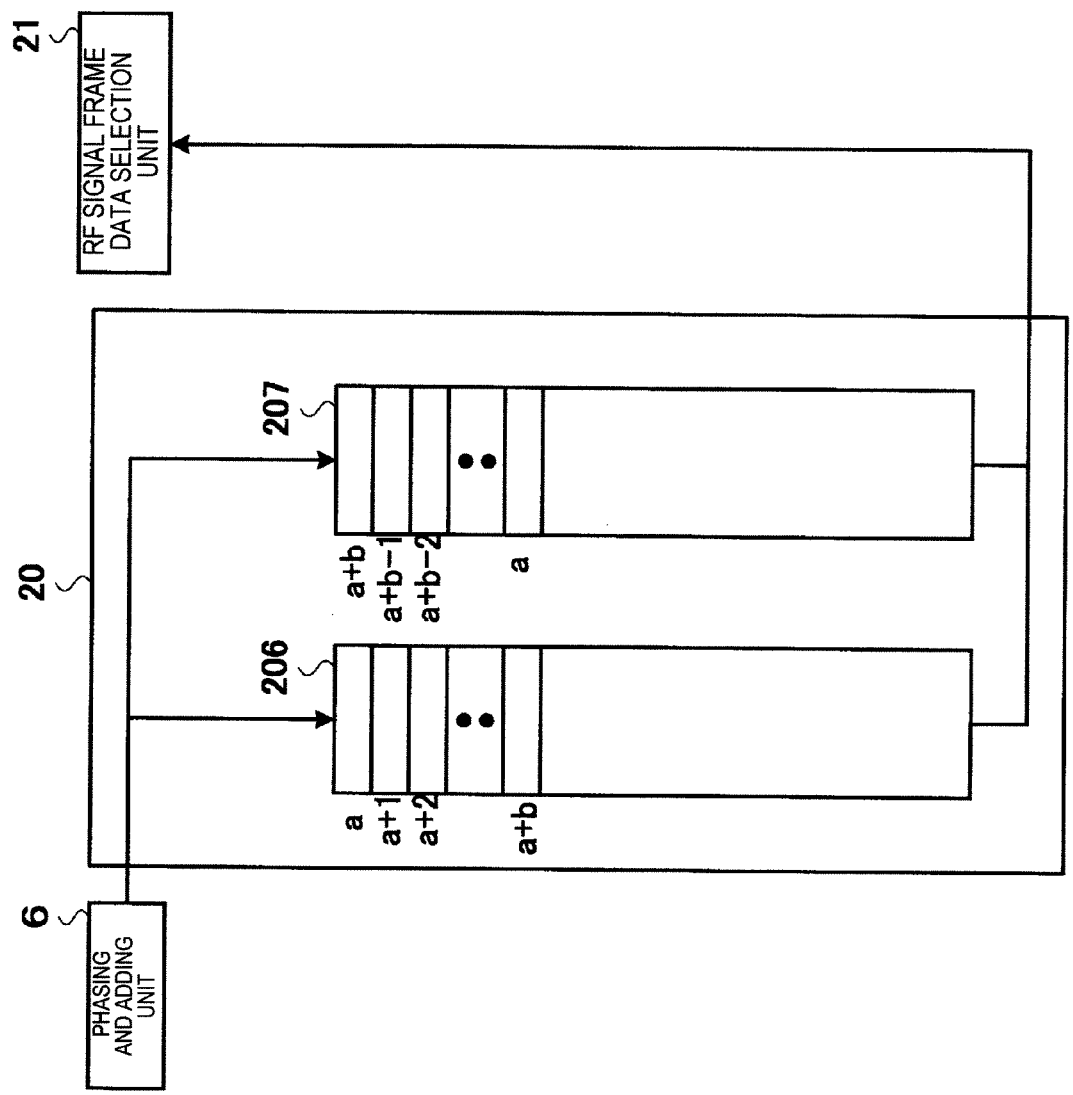
FIG. 11 shows details of the RF signal frame data storing unit in a sixth embodiment of the present invention.
Figure 12:
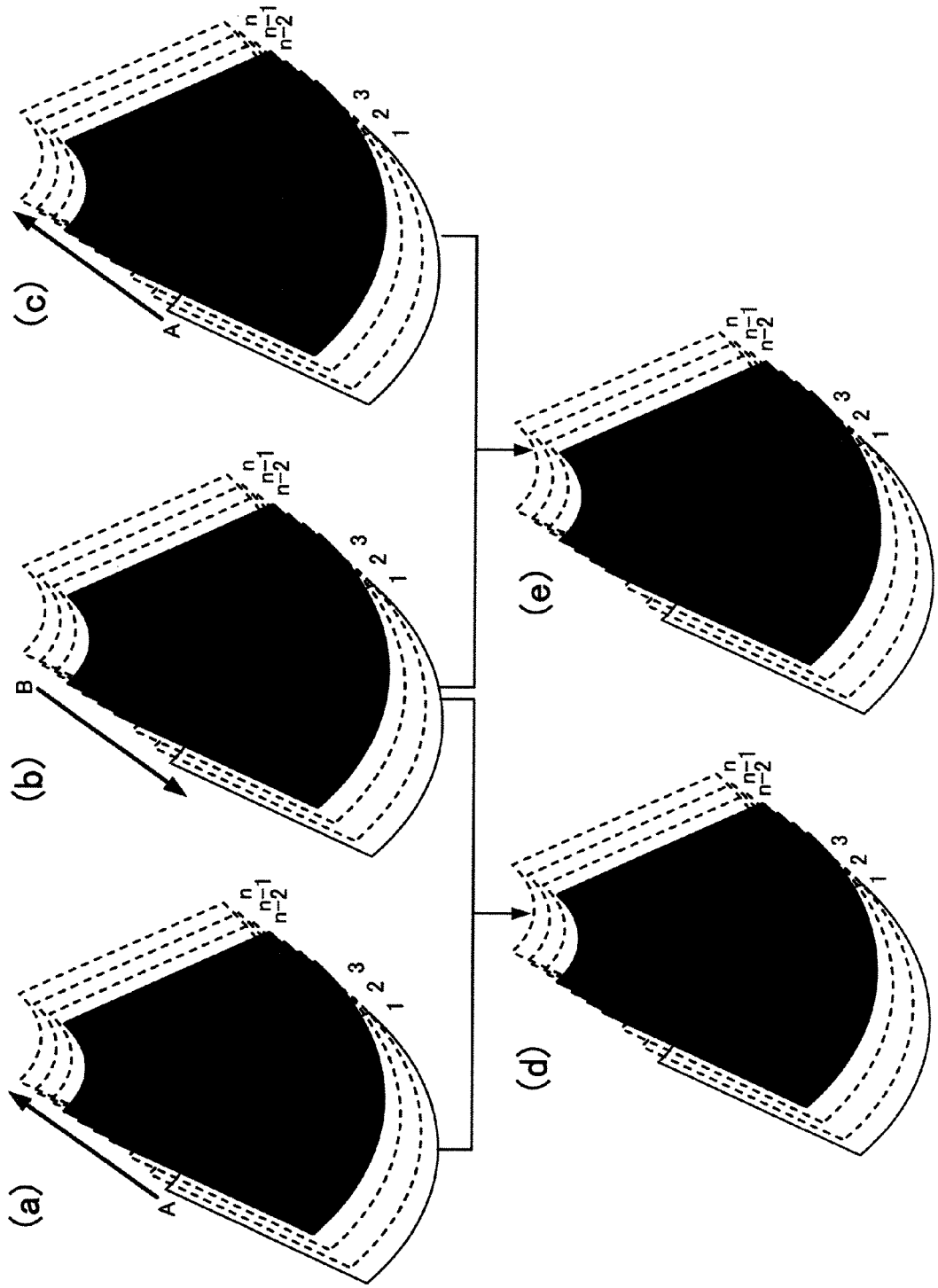
FIG. 12 shows the pattern for creating 2-dimensional elastic image data in the sixth embodiment of the present invention.

As shown in FIG. 11, storage media 206 stores the RF signal frame data within a predetermined range of the scan in A-direction. Storage media 206 sets the first frame number as "a" and the last frame number as "a+b", and stores the RF signal frame data between them. The "a" and "a+b" are integers of 1~n. In the same manner, storage media 207 also sets the first frame number of the scan in B-direction as "a+b" and the last frame number as "a", and stores the RF signal frame data of a predetermined range.

RF signal frame data selecting unit 21 selects the RF signal frame data of the same frame numbers "a"~"a+b" stored in storage media 206 and storage media 207 of RF signal frame data storing unit 20 respectively, and executes a series of processing as described above in displacement measuring unit 22, elasticity information calculating unit 23, elastic image constructing unit 24 and elasticity scan converter 25. Explanation on the above-mentioned processing will be omitted here since it is the same as in the first embodiment.

2-dimensional elastic image storing unit 26 stores the 2-dimensional elastic image data of frame numbers "a" "a+b". FIG. 12 shows the pattern for creating 2-dimensional elastic image data with frame numbers "a"~"a+b". FIGS. 12(a) and (b) show the pattern that the RF signal frame data of frame numbers "a"~"a+b" in A-direction or B-direction is read out from storage media 205 and storage media 206, and FIG. 12(d) shows the condition that the 2-dimensional elastic image data of frame numbers "a"~"a+b" is stored in 2-dimensional elastic image storing unit 26.

Then as shown in FIG. 12(c), when the scanning is newly executed in A-direction, the RF signal frame data of frame numbers "a"~"a+b" stored in storage media 206 is re-written with RF signal frame data of frame numbers "a"~"a+b" of the time when the scanning is newly executed in A-direction. Then the RF signal frame data of the same frame numbers "a"~"a+b" in A-direction and B-direction is read out from storage media 206 and storage media 207 as shown in FIGS. 12(b) and (c), elasticity calculation is executed as in the same pattern of FIG. 12(d) as shown in FIG. 12(e), and the 2-dimensional elastic image data of frame numbers "a"~"a+b" is stored in 2-dimensional elastic image storing unit 26. Also, the same processing is to be executed when the scanning is newly executed in B-direction, wherein the scanning in A-direction and B-direction is sequentially executed and the 2-dimensional elastic image data of frame number "a"~"a+b" is sequentially stored in 2-dimensional elastic image storing unit 26.

Elastic volume data creating unit 27 creates elastic volume data from plural sets of 2-dimensional elastic image data. It reads out the 2-dimensional elastic image data for the portion of b-frame stored in 2-dimensional elastic image storing unit 26, and creates elastic volume data by sequentially disposing the data for each scan plane. In this manner, elastic volume data for rendering that is the collection of 2-dimensional elastic image data in an object is constructed.

Also, 3-dimensional elastic image constructing unit 28 acquires image information on each point of the elastic volume data from the elasticity value and the opacity corresponding to the respective points. Then it constructs a 3-dimensional elastic image using the volume rendering method which calculates an elasticity value of the elastic volume data of the view point direction in the depth direction.

The image memory of switching and synthesizing unit 12 stores the black and white 3-dimensional tomographic image of frame numbers "1"~"n" outputted from black and white 3-dimensional tomographic image constructing unit 11 and the color 3-dimensional elastic image of frame numbers "a"~"a+b" outputted from color 3-dimensional elastic image constructing unit 28 along with time information. Also, the image processing unit synthesizes the black and white 3-dimensional tomographic image data stored in the image memory and the color 3-dimensional elastic image data by changing the synthesizing, ratio within the range of frame numbers "a"~"a+b". Image display unit 13 displays the image synthesized by switching and synthesizing unit 12. Frame numbers "a"~"a+b" can be arbitrarily set via input unit 30.

In accordance with the present embodiment, it is possible to reduce the amount of elasticity calculation by partially constructing a 3-dimensional elastic image. Also, only the significant 3-dimensional elastic image of the area concerned can be displayed.

DESCRIPTION OF REFERENCE NUMERALS

1: object, 2: ultrasonic probe, 3: transmission unit, 4: reception unit, 5: ultrasonic transmission/reception control unit, 6: phasing and adding unit, 7: tomographic image constructing unit, 8: black and white scan converter, 9: 2-dimensional tomographic image storing unit, 10: black and white volume data creating unit, 11: black and white 3-dimensional tomographic image constructing unit, 12: switching and synthesizing unit, 13: image display unit, 20: RF signal frame data storing unit, 21: RF signal frame data selecting unit, 22: displacement calculating unit, 23: elasticity information calculating unit, 24: elastic image constructing unit, 25: color scan converter, 26: 2-dimensional elastic image storing unit, 27: elastic volume data creating unit, 28: color 3-dimensional elastic image constructing unit

The invention claimed is:

1. An ultrasonic diagnostic apparatus comprising:
an ultrasonic probe having transducers that transmit/receive ultrasonic waves;
a computer including a processor and storage, pre-configured to implement operations including:
transmitting ultrasonic waves to an object to be examined, via the ultrasonic probe;
receiving reflected echo signals from the object;
storing RF signal frame data based on the reflected echo signals received by the receiving, in the storage which includes:
a first storage media that stores a first series of the RF signal frame data scanned by hand movement in a first direction of a first sweep of the ultrasound probe along a sweep line; and
a second storage media that stores a second series of the RF signal frame data scanned by hand movement in a second direction of a second sweep of the ultrasound probe along the sweep line;

selecting at least a pair of the first and second series of the RF signal frame data stored in the first and second storage media, respectively, of the storage;

calculating strain or elasticity modulus, based on the selected RF signal frame data from the selecting;

constructing 2-dimensional elastic image frame data, based on the strain or the elasticity modulus obtained by the calculating strain or elasticity modulus;

creating elastic volume data from plural sets of the 2-dimensional elastic image frame data from the constructing 2-dimensional elastic image frame data, by comparison of the first and the second series of the RF signal frame data obtained at a substantially same position of the ultrasound probe along the sweep line; and constructing 3-dimensional elastic image from the elastic volume data created by the creating.

2. The ultrasonic diagnostic apparatus according to claim 1, wherein the ultrasonic probe is configured such that transducers can be tilted in the direction orthogonal to their array direction.

3. The ultrasonic diagnostic apparatus according to claim 2, wherein the ultrasonic probe has a position sensor that measures tilt of the transducers and outputs the measured tilt of the transducers as a frame number.

4. The ultrasonic diagnostic apparatus according to claim 1, wherein the first and second storage media store respectively the first and second series of the RF signal frame data scanned by hand movement in one direction, along with a frame number corresponding to the tilt of the transducers.

5. The ultrasonic diagnostic apparatus according to claim 4, wherein, in the case that scan by hand movement is newly executed in one direction, the RF signal frame data stored in the storage media is re-written to the RF signal frame data of the newly executed scan.

6. The ultrasonic diagnostic apparatus according to claim 4, wherein the selecting selects the RF signal frame data having the same frame number from the first storage media and the second storage media of the RF signal frame data storing unit.

7. The ultrasonic diagnostic apparatus according to claim 4, wherein the selecting selects the at least a pair of the first and second series of the RF signal frame data of the scan in the first direction of the first sweep of the ultrasound probe and the second direction of the second sweep of the ultrasound probe, respectively, where the first direction and the second direction are same directions.

8. The ultrasonic diagnostic apparatus according to claim 4, wherein in the case that a scan by hand movement is newly executed in the first direction, the first storage media re-writes the first series of the RF signal frame data, and in the case that a scan by hand movement is newly executed in the second direction, the second storage media re-writes the second series of the RF signal frame data.

9. The ultrasonic diagnostic apparatus according to claim 1, wherein the selecting selects the at least a pair of the first and second series of the RF signal frame data of the scan in the first direction of the first sweep of the ultrasound probe and the second direction of the second sweep of the ultrasound probe, respectively, where the first direction and the second direction are opposite directions.

10. The ultrasonic diagnostic apparatus according to claim 1, wherein the constructing 3-dimensional elastic image adjusts opacity of the 3-dimensional elastic image according to the strain or the elasticity modulus.

11. The ultrasonic diagnostic apparatus according to claim 1, wherein:

the storing the RF signal frame data stores the RF signal frame data within a predetermined range from among a series of RF signal frame data that is scanned in one direction along with the frame number corresponded to the tilt of the transducers; and the constructing 3-dimensional elastic image constructs the 3-dimensional elastic image using RF signal frame data within the predetermined range.

12. The ultrasonic diagnostic apparatus according to claim 1, wherein the selecting the RF signal frame data selects at least one frame of the RF signal frame data of the scan in the first direction of the first sweep of the ultrasound probe, and at least one frame of the scan in the second direction of the second sweep of the ultrasound probe, wherein the first direction and the second direction are opposite directions.

13. The ultrasonic diagnostic apparatus according to claim 1, wherein the computer is pre-configured to implement further operations including:

constructing tomographic image data from the RF signal frame data;

creating tomographic volume data from plural sets of the tomographic image data; and constructing a 3-dimensional tomographic image from the tomographic volume data.

14. The ultrasonic diagnostic apparatus according to claim 13, wherein the constructing 3-dimensional elastic image from the tomographic volume data, acquires, from the calculating strain or elasticity modulus, image information of each point of the elastic volume data based on the strain or the elasticity modulus corresponding to the respective points, and constructs the 3-dimensional elastic image.

15. The ultrasonic diagnostic apparatus according to claim 13, wherein the computer is pre-configured to implement further operations including:

acquiring image information on each point of composite volume data in which the elastic volume data and tomographic volume data are synthesized from calculated luminance and elasticity values corresponding to the respective points.

16. An ultrasonic diagnostic apparatus comprising:

an ultrasonic probe having transducers that transmit/receive ultrasonic waves;

a computer including a processor and storage, pre-configured to implement operations including:

transmitting ultrasonic waves to an object to be examined, via the ultrasonic probe;

receiving reflected echo signals from the object;

storing RF signal frame data, based on the reflected echo signals received by the receiving, in the storage which includes:

a first storage media that stores a first series of the RF signal frame data scanned by hand movement in a first direction of a first sweep of the ultrasound probe along a sweep line across a surface of the object; and a second storage media that stores a second series of the RF signal frame data scanned by hand movement in a second direction of a second sweep of the ultrasound probe along the sweep line across the surface of the object, the second direction is the same as or opposite to the first direction;

selecting at least a pair of the first and second series of the RF signal frame data stored in the first and second storage media, respectively, of the storage;

calculating strain or elasticity modulus, based on the selected RF signal frame data from the selecting;

constructing 2-dimensional elastic image frame data, based on the strain or the elasticity modulus obtained by the calculating strain or elasticity modulus;

creating elastic volume data from plural sets of the 2-dimensional elastic image frame data from the constructing 2-dimensional elastic image frame data, by comparison of the first and the second series of the RF signal frame data obtained at a substantially same position of the ultrasound probe along the sweep line; and constructing a 3-dimensional elastic image from the elastic volume data created by the creating.

17. The ultrasonic diagnostic apparatus according to claim 16, wherein the selecting the RF signal frame data selects at least one frame of the RF signal frame data of the scan in the first direction of the first sweep of the ultrasound probe, and at least one frame of the scan in the second direction of the second sweep of the ultrasound probe, wherein the first direction and the second direction are opposite directions.

18. An ultrasonic image display method comprising:

applying an ultrasonic probe having transducers that transmit/receive ultrasonic waves, to a surface of an object to be examined; and a computer including a processor and storage, implementing operations including:

transmitting ultrasonic waves to the object, via the ultrasonic probe;

receiving reflected echo signals from the object;

storing RF signal frame data based on the reflected echo signals received by the receiving operation in the storage which includes:

a first storage media that stores a first series of the RF signal frame data scanned by hand movement in a first direction of a first sweep of the ultrasound probe along a sweep line; and a second storage media that stores a second series of the RF signal frame data scanned by hand movement in a second direction of a second sweep of the ultrasound probe along the sweep line;

selecting at least a pair of the first and second series of the RF signal frame data stored in the first and second storage media, respectively, of the storage;

calculating strain or elasticity modulus based on the selected RF signal frame data;

constructing 2-dimensional elastic image frame data based on the strain or the elasticity modulus obtained by the calculating operation;

creating elastic volume data from plural sets of the 2-dimensional elastic image frame data from the constructing 2-dimensional elastic image frame data, by comparison of the first and the second series of the RF signal frame data obtained at a substantially same position of the ultrasound probe along the sweep line; and constructing a 3-dimensional elastic image from the elastic volume data created by the creating operation.

19. The ultrasonic image display method according to claim 18, wherein the selecting the RF signal frame data selects at least one frame of the RF signal frame data of the scan in the first direction of the first sweep of the ultrasound probe, and at least one frame of the scan in the second direction of the second sweep of the ultrasound probe, wherein the first direction and the second direction are opposite directions.

* * * * *